United States Patent
Godin

(10) Patent No.: US 11,980,539 B2
(45) Date of Patent: May 14, 2024

(54) THERAPEUTIC-GARD AND METHOD OF USE THEREOF

(71) Applicant: BIOMEDIX, S.A., Geneva (CH)

(72) Inventor: Norman Godin, Geneva (CH)

(73) Assignee: BIOMEDIX, S.A., Geneva (CH)

( * ) Notice: Subject to any disclaimer, the term of this patent is extended or adjusted under 35 U.S.C. 154(b) by 868 days.

(21) Appl. No.: 16/965,281

(22) PCT Filed: Feb. 12, 2019

(86) PCT No.: PCT/IB2019/000137
§ 371 (c)(1),
(2) Date: Jul. 27, 2020

(87) PCT Pub. No.: WO2019/155284
PCT Pub. Date: Aug. 15, 2019

(65) Prior Publication Data
US 2021/0068940 A1    Mar. 11, 2021

Related U.S. Application Data

(60) Provisional application No. 62/629,216, filed on Feb. 12, 2018.

(51) Int. Cl.
*A61F 2/04*          (2013.01)

(52) U.S. Cl.
CPC .......... *A61F 2/04* (2013.01); *A61F 2002/044* (2013.01); *A61F 2210/0014* (2013.01)

(58) Field of Classification Search
CPC .................. A61F 2/04; A61F 2002/044; A61F 2210/0014; A61F 5/0073; A61F 2/2412; A61F 5/0076
See application file for complete search history.

(56) References Cited

U.S. PATENT DOCUMENTS

| | | | |
|---|---|---|---|
| 6,254,642 B1 * | 7/2001 | Taylor | A61F 2/2476 623/23.64 |
| 9,622,897 B1 | 4/2017 | Stangenes et al. | |
| 2003/0040808 A1 | 2/2003 | Stack et al. | |
| 2009/0093767 A1 | 4/2009 | Kelleher | |
| 2010/0256775 A1 | 10/2010 | Belhe et al. | |
| 2016/0000549 A1 | 1/2016 | Gittard et al. | |

FOREIGN PATENT DOCUMENTS

| | | |
|---|---|---|
| WO | 2008018849 A2 | 2/2008 |
| WO | 2009100313 A1 | 8/2009 |

OTHER PUBLICATIONS

International Search Report and Written Opinion of PCT/IB2019/000137 dated Jul. 23, 2019.

* cited by examiner

*Primary Examiner* — Yashita Sharma
(74) *Attorney, Agent, or Firm* — Debora Plehn-Dujowich; Mark T. Vogelbacker; Eckert Seamans Cherin & Mellott, LLC

(57) ABSTRACT

A prosthesis used for long-term treatment of Gastro-Esophageal Reflux Disease (GERD) comprising an upper thin ring mesh for incorporation in the esophageal wall with a lower tubular part to block reflux and a method where a temporary ring is placed to exert compression laterally on a thin ring supporting a tubular or slit valve to treat GERD to help the thin ring incorporate in the esophageal wall.

6 Claims, 12 Drawing Sheets

THERAPEUTIC-GARD AND METHOD OF USE THEREOF

CROSS-REFERENCE TO RELATED APPLICATION

The present application is a 35 U.S.C. § 371 national phase application from International Application No. PCT/IB2019/000137, filed Feb. 12, 2019, and published under PCT Article 21(2) in English, which designated the U.S., and claims the benefit of priority from U.S. Provisional Application Ser. No. 62/629,216, filed Feb. 12, 2018 and each of which prior applications are incorporated by reference herein into this application in their entirety including all tables, figures and claims.

BACKGROUND OF THE INVENTION

In U.S. Pat. No. 10,085,867 B2, a Gastro-intestinal Anti-Reflux Device (GARD) which functions as an anti-obesity device within a human gastro-intestinal tract, the device comprising an elastic portion including a helical elastic spring embedded in a biocompatible material. This device works well as a temporary device placed up to one month in the esophagus or a hiatus hernia of a patient who has reflux esophagitis or refractory GERD, that is patients who do not respond to Proton pump inhibitors, a class of drugs used for that indication.

SUMMARY OF THE INVENTION

By placing a temporary device called the Diagnosis and Management GARD (DM-GARD) in a patient, it is possible to find out if the patient's symptoms are relieved by the DM-GARD device and if placing a GARD device for long-term implantation is recommended.

For long-term implantation the ring of the device has to be embedded in the mucosa of the esophagus, which the DM-GARD does not do and so a prior art GARD risks migration and falling in the stomach even when Botulinum Toxin is injected.

In one aspect of the invention, a ring made of a biocompatible mesh or net such as polypropylene, polyethylene, or polytetrafluoroethylene in the upper part of the device that is glued, sutured or stapled but preferably glued using a biocompatible glue such as a cyanoacrylate to an anti-reflux tube as described in U.S. Pat. No. 5,861,036 of Jan. 19, 1999 or a slit tube as previously described and as shown in FIGS. 11b and 12 of U.S. Pat. Publ. 2007/0027549 A1.

DETAILED DESCRIPTION OF THE INVENTION AND THE PREFERRED EMBODIMENTS

Surgical nets or meshes have been used for many years for inguinal hernia repair but the surgeon does not induce bleeding to attach the net with the coagulation and scarring process induced in the patient as we do.

In U.S. Pat. No. 10,085,867, a net is described which is glued on the helical spring ring and when the device is implanted, bleeding is induced with biopsies. However, the thickness of the ring with the incorporated nitinol spring is at least 1 mm to 2 mm thick which is too thick to expect the ring to be embedded in an esophageal mucosa that is about 0.5 mm thick. Also, the thicker helical spring ring can also interfere with food passing through the esophagus, particularly with bigger bolus of food containing bread or meat.

According to the present invention a new medical device using only a ring made of a net or mesh that is about 0.1 mm thick so at least 10 to 20 times thinner than the prior art ring is used. This makes a major difference as the net can be incorporated in the esophageal mucosa and hold the anti-reflux tubes, slit or not in place as well as longer tubes reaching the stomach and mimicking a common anti-obesity operation, namely the "sleeve gastrectomy," but without surgery, by passing through the mouth and without gastrectomy, that is cutting out three-quarters of the stomach.

Figure 8:
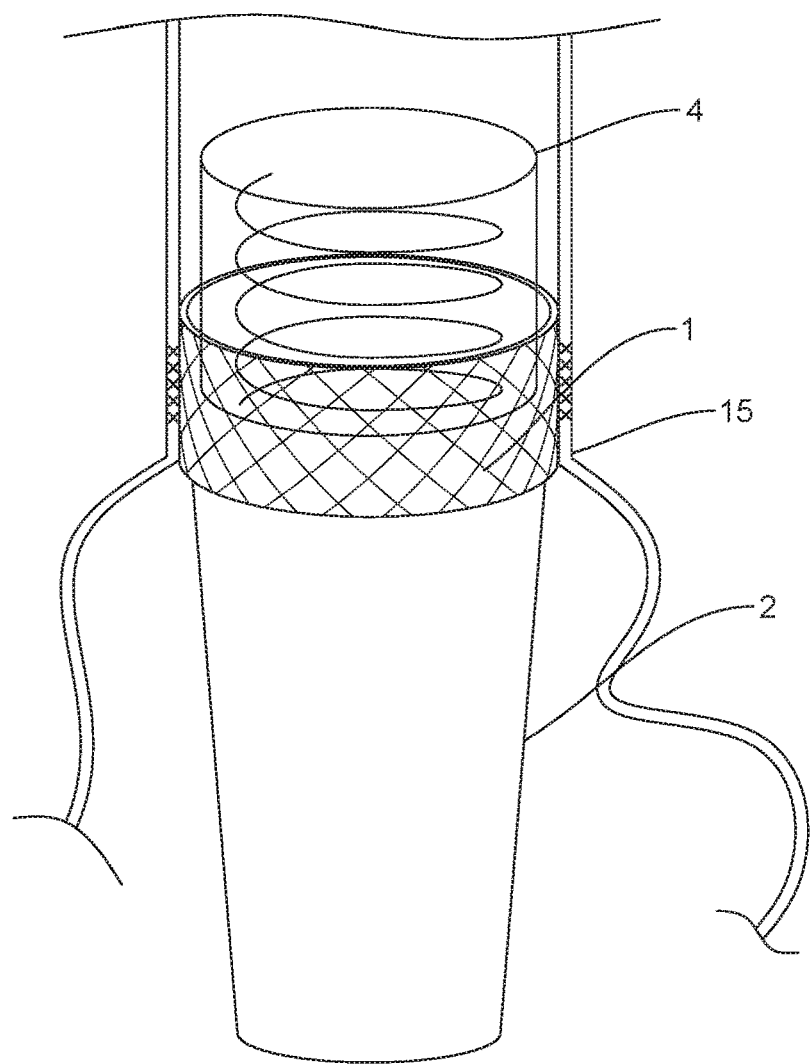
FIGS. 8 and 8a show positioning of the mesh ring on the bleeding sites on the esophageal mucosa.
Figure 11A:
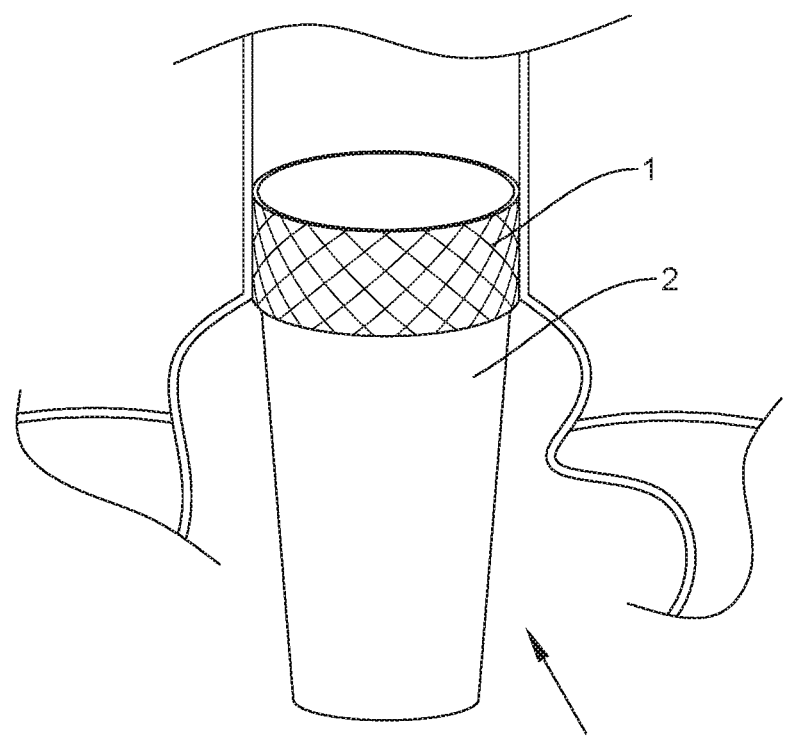
FIG. 11a shows a mesh ring integrated in the esophageal wall with a tubular valve.

A helical spring will still be used temporarily to exert lateral pressure on the net but will not be glued or bound to the net and will be removed through the mouth after a few days or weeks as described in FIG. 8, leaving the incorporated net in the esophageal wall with the underlying anti-reflux tubes in place (FIG. 11a).

The fact of having a thin net alone as a final ring for the Therapeutic GARD without a permanent helical spring ring makes a huge difference as the anti-reflux tubes can now be left in place for years, which is not the case with the helical spring alone that cannot be incorporated in the esophageal wall because it was too thick.

In addition, careful calibration of the diameter of the esophagus at the location of implantation is necessary. The calibration basket described in FIG. 2 of U.S. Pat. No. 10,085,867 is not sufficiently precise to determine exact diameter and had to be replaced by a calibration balloon filled with air or water. See FIG. 3 of this patent application.

Figure 4A:
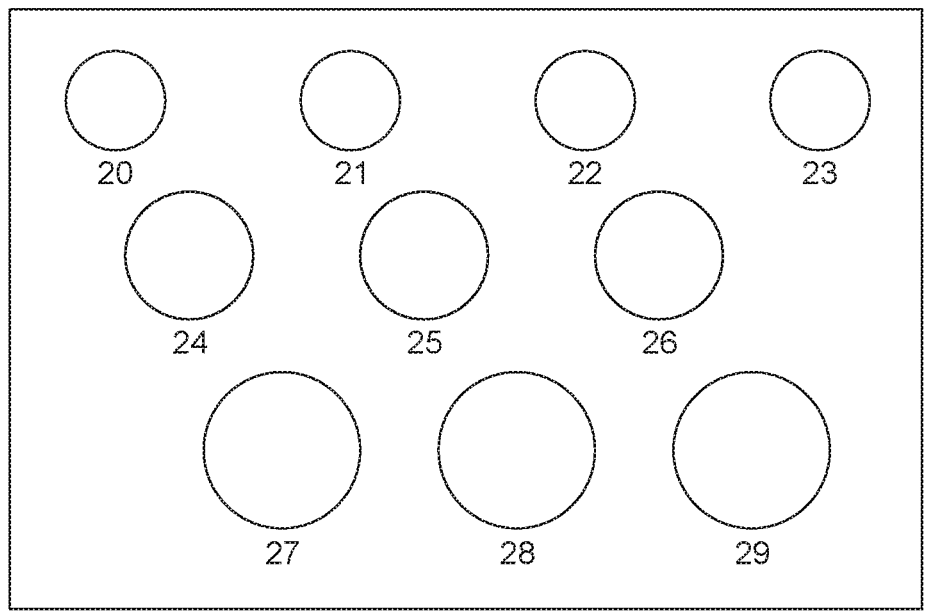
FIGS. 4a and 4b show a calibration card.
Figure 4B:
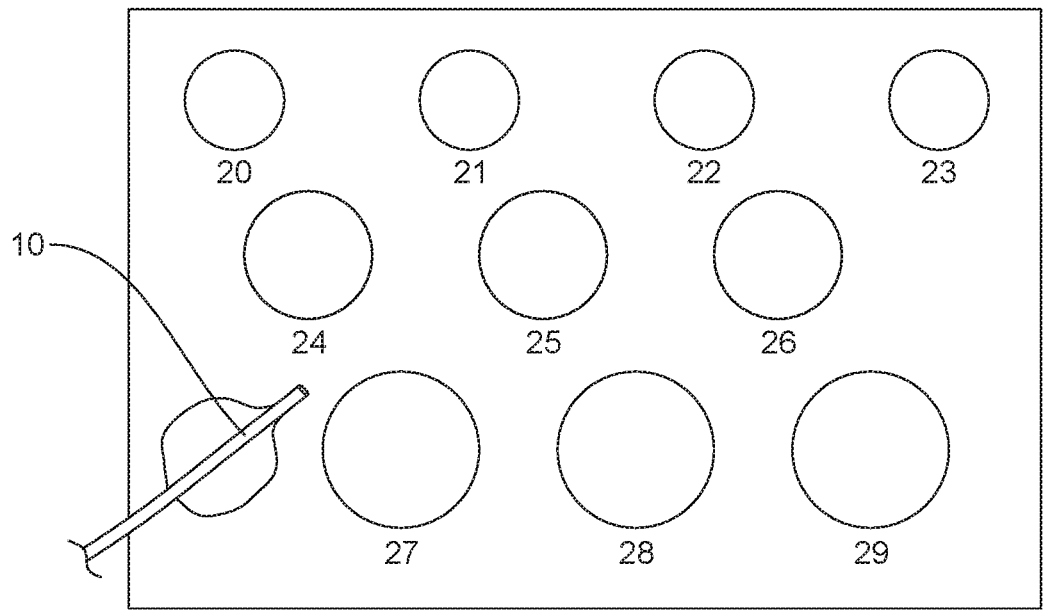

According to another aspect of the present invention air is injected into a calibrator balloon and the volume of air injected is exactly measured to determine the volume needed to inflate the calibration balloon until it reaches the wall of the esophagus. A manometer can be used and as soon as pressure in the balloon starts to increase the volume inflated is determined, the balloon deflated and pulled out of the esophagus. Outside of the patient the balloon is reinflated with exactly the same volume of air and the diameter of the mesh is obtained by comparing in a calibration card the diameter of the calibration balloon with 10 diameters between 20 mm and 30 mm on the calibration card as shown in FIGS. 4a and 4b so as to determine the exact size of the mesh ring needed for a particular patient. If the size of the inflated balloon is between 2 sizes the larger diameter of the 2 holes is chosen.

Figure 5:
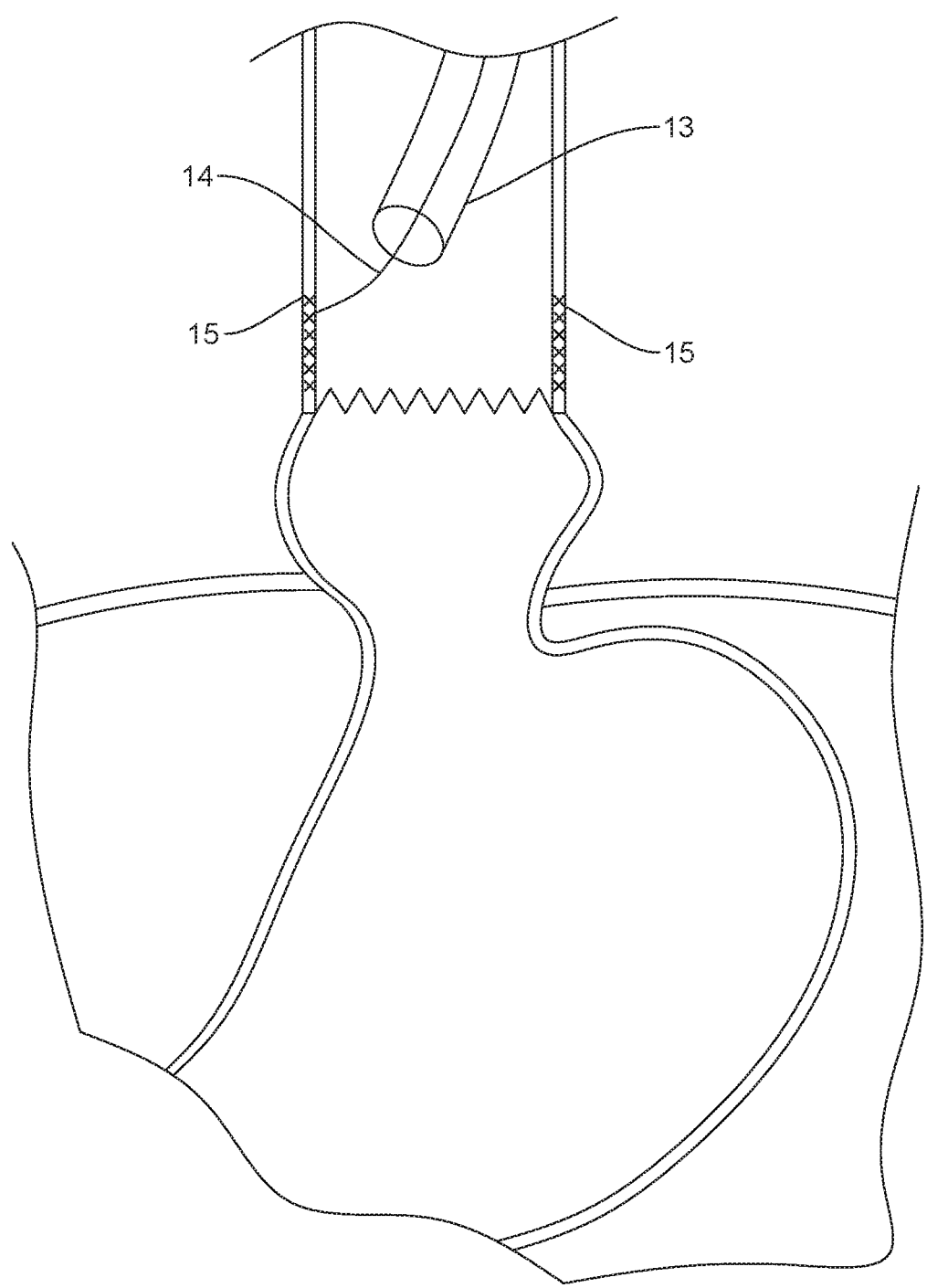
FIG. 5 illustrates an endoscope (13) with a biopsy catheter used to make multiple biopsies of the esophageal mucosa (15) above the hiatus hernia.
Figure 6:
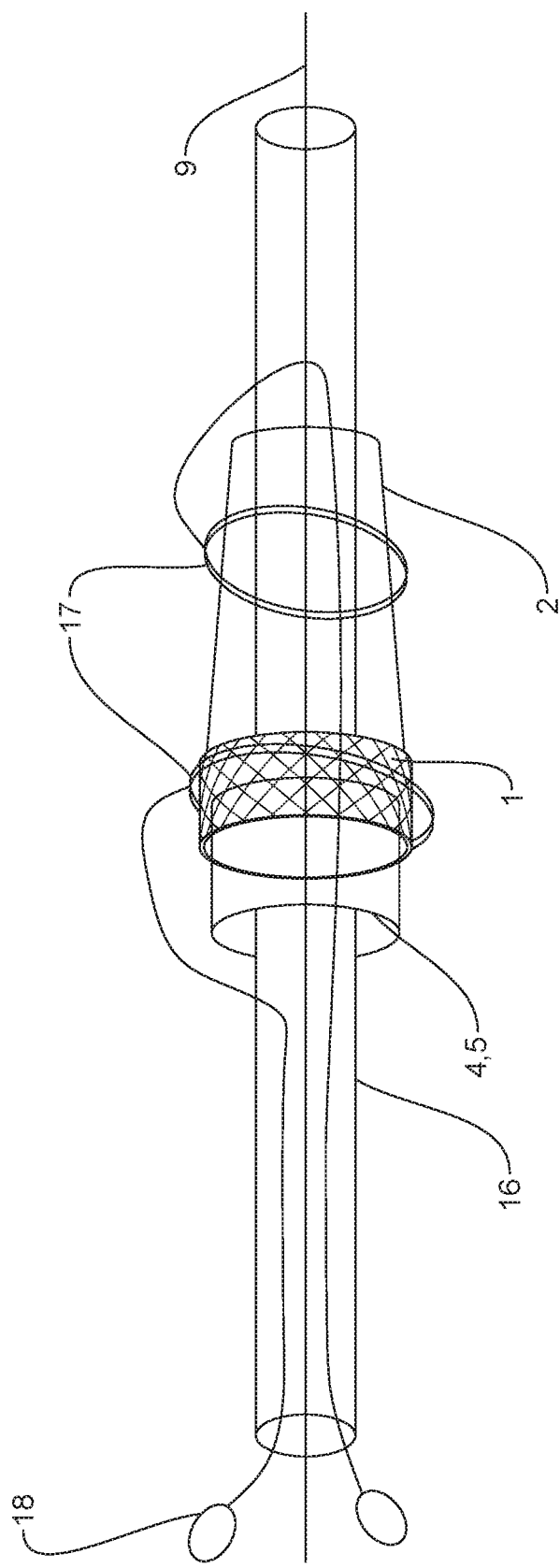
FIG. 6 shows Therapeutic-GARD of the invention folded on an introducer catheter which has a central hole for the guide-wire.
Figure 7:
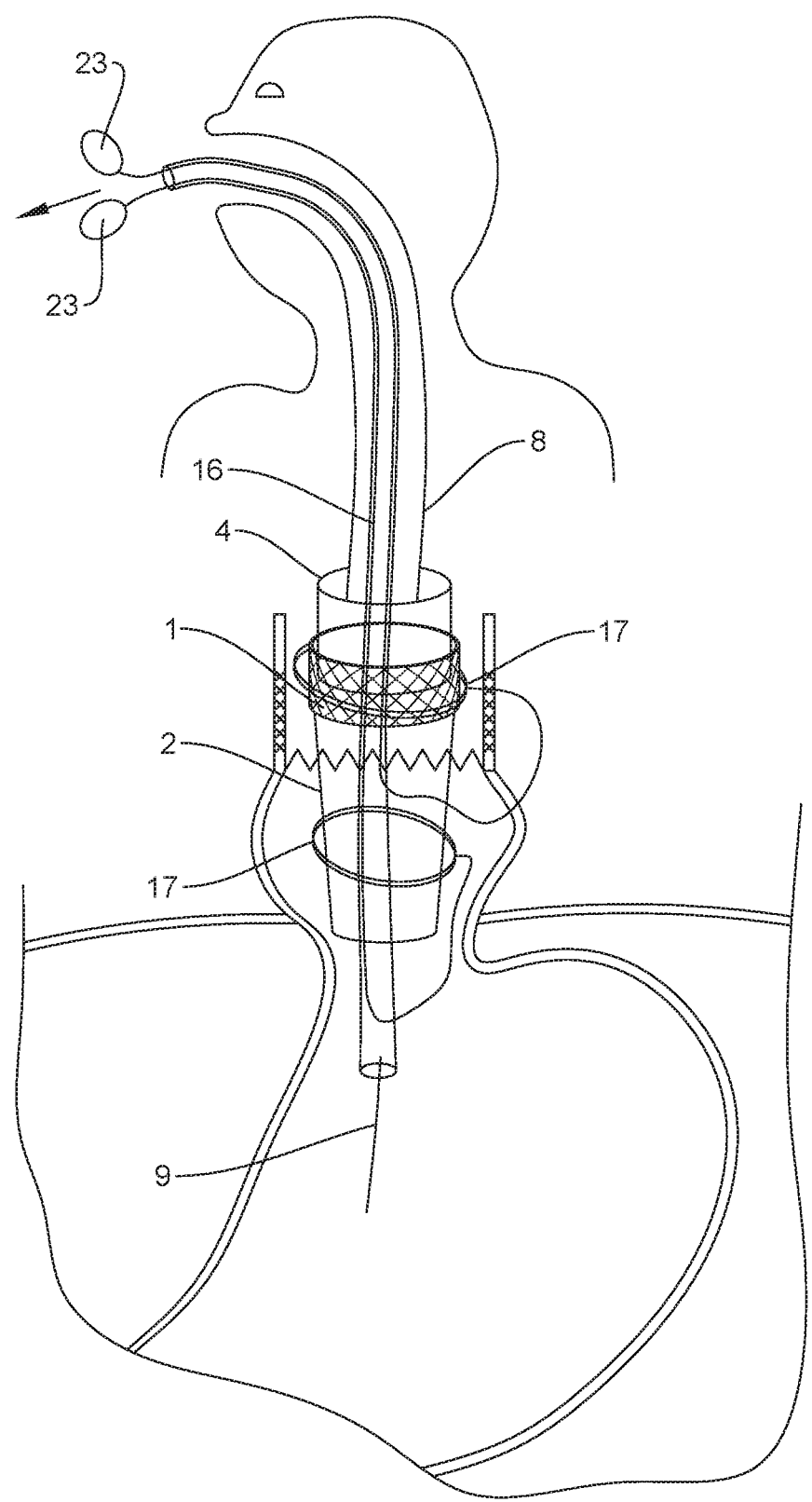
FIG. 7 illustrates the Therapeutic-GARD of FIG. 6 in a patient's esophagus.

Once the exact size of the Therapeutic-GARD is obtained, the appropriate size Therapeutic-GARD is inserted over a guide wire and after that approximately a dozen biopsies are taken around the diameter of the esophagus over about 2 cm portion in height of the esophagus immediately above the Z line or endoscopic mucosal resection (EMR) or possible endoscopic submucosal dissection (ESD) can be used (FIG. 5). The Therapeutic-GARD is then inserted as shown in FIG. 6 and FIG. 7 and the mesh is in direct contact with the bleeding mucosa as demonstrated in FIG. 8. The nitinol spring ring will exert lateral pressure on the net to help integration of the mesh in the bleeding mucosa that will then coagulate and heal over the mesh ring holding the tubular valve underneath it.

Figure 9:
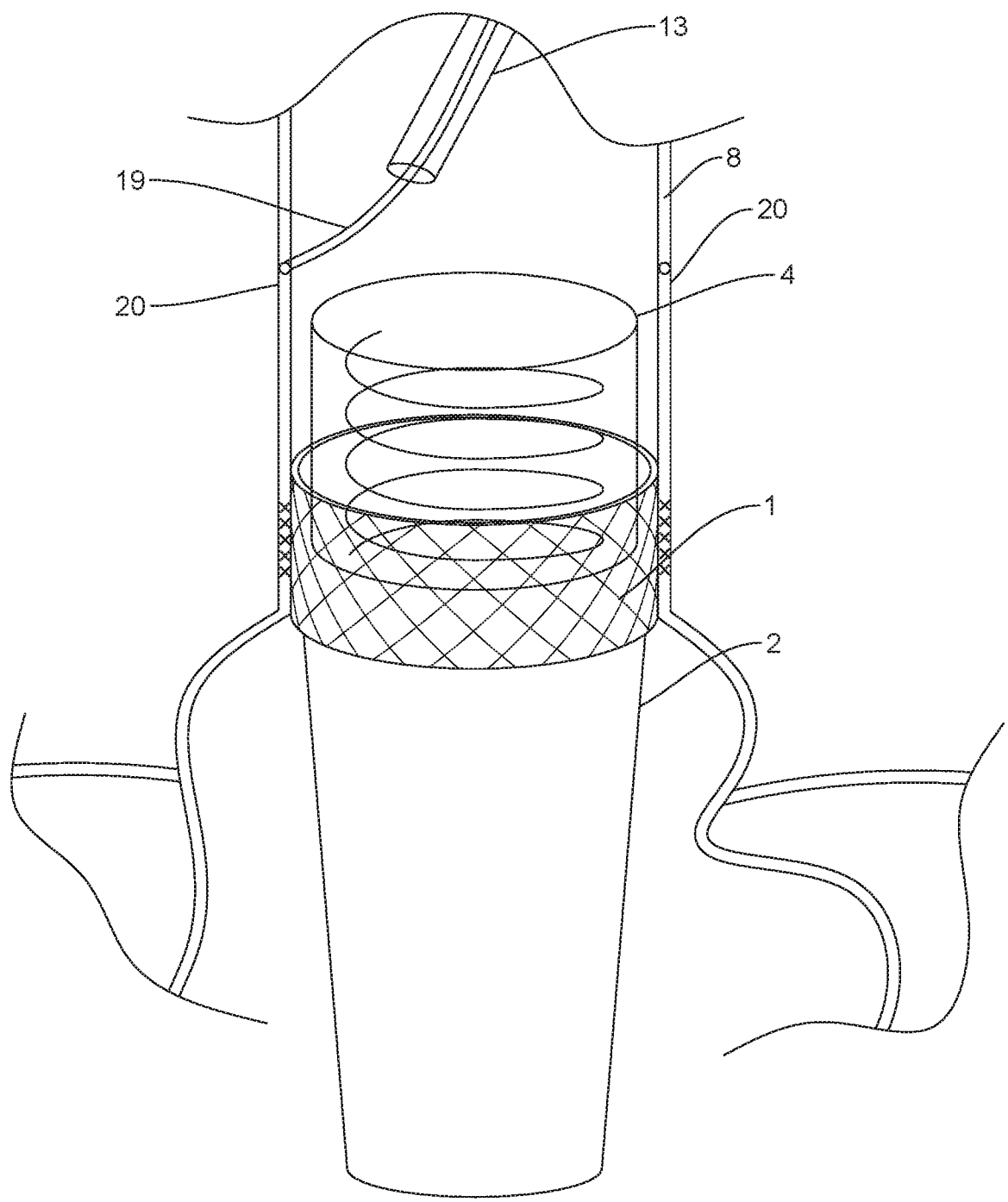
FIG. 9 shows injection using an endoscope with an injection catheter of botulinum toxin that blocks peristalsis in the esophageal wall.

Then as illustrated in FIG. 9, botulinum toxin is injected in the mucosa right above the nitinol spring ring to block peristalsis locally and help the mesh integrate the wall of the esophagus. Anytime after 1 to 4 weeks of implantation, the nitinol spring ring that rises above the mesh ring for easier grasp with the removal forceps provided with a thin guide-wire blocked between the mucosa and the side of the nitinol spring ring that helps grasping the side of the nitinol spring ring to remove the ring gently out of the body. Without the thin guide-wire (not shown in FIG. 10), it would be harder to grasp the side of the nitinol spring ring as the grasping forceps tends to remain in the center of the ring. More than one removal forceps can be used at a time to remove the ring safely.

During the days and weeks of implantation, an anti-nauseous drug such as metoclopramide and/or domperidone or an anti-emetic (anti-vomiting) drug such as ondansetron can be prescribed.

Figure 11B:
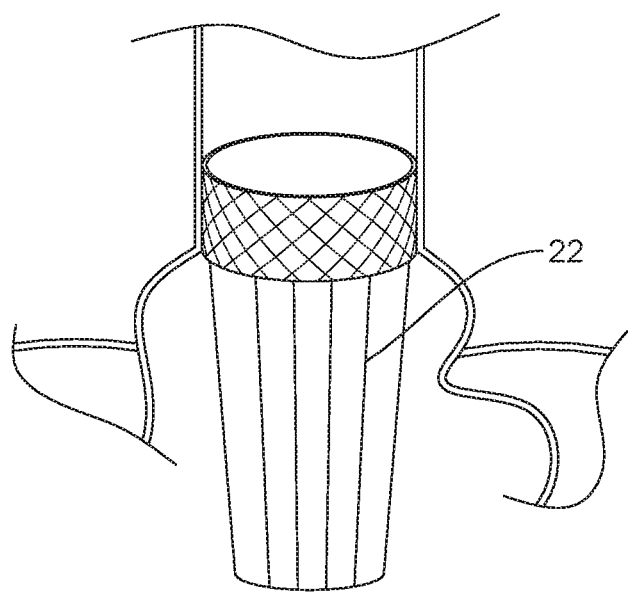
FIG. 11b illustrates the device of FIG. 11a with a slit valve allowing vomiting as shown when the slit valve reverses as in FIG. 11c.

In FIGS. 11a and 11b, the end result is demonstrated with the mesh ring incorporated with the tubular valve that blocks all refluxate and the slit valve that is a little less effective in blocking reflux but has the added advantage of allowing vomiting and resuming the original position after vomiting (FIG. 11b). The choice for the clinician between the tubular valve and the slit valve (FIG. 12) will depend if the patient has had vomiting episodes in the previous years as well as the severity of GERD symptoms. For patients who need 20 mg to 40 mg of PPIs to control their reflux symptoms daily, the slit Therapeutic-GARD should be sufficient. For patients with more severe symptoms who need 40 mg to 80 mg of PPIs a day, the tubular Therapeutic-GARD will be indicated. There is always the possibility of using the DM-GARD with either a tubular valve of a slit valve for temporary implantation to determine which model is best for a given patient.

In order to reinforce integration of the mesh in the esophageal wall after the nitinol spring ring is removed, local use of a Fibrin sealant or other glues remains an option to help coagulation and scarring.

Figure 1:
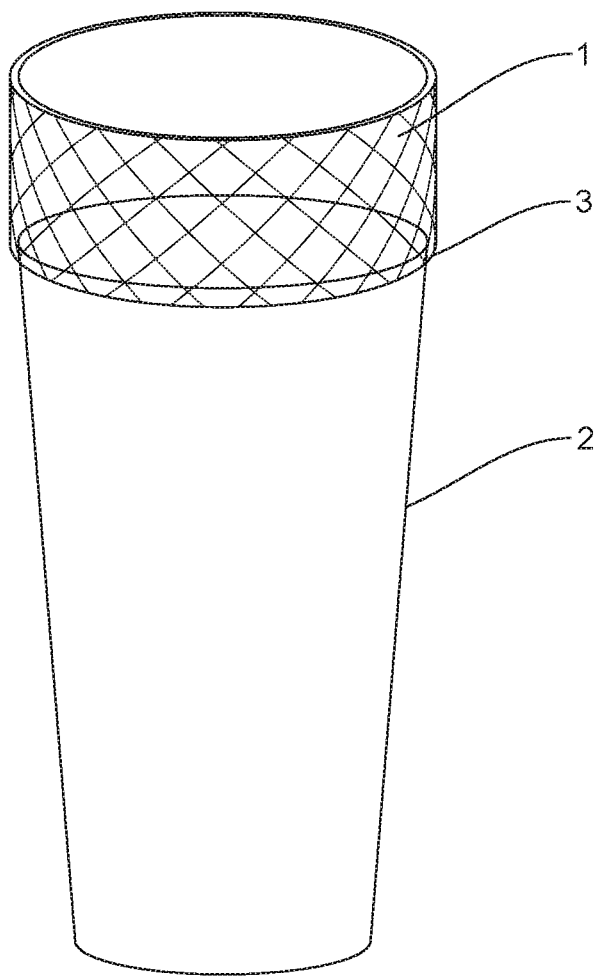
FIG. 1 illustrates an embodiment of a Therapeutic-GARD according to the invention.

Referring now to the drawings, FIG. 1 illustrates a Therapeutic-GARD according to the invention wherein thin mesh ring 1, tubular silicone valve 2 and the area 3 where the mesh is covering the silicone ring is carefully glued to the silicone ring on a short 5 mm to 10 mm surface.

Figure 2:
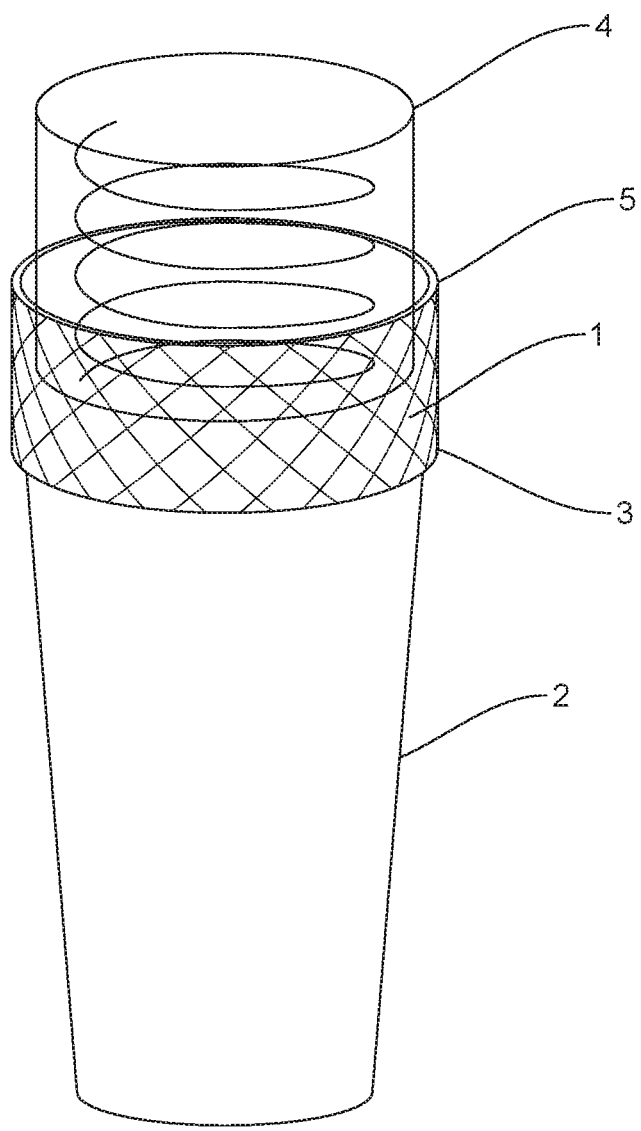
FIG. 2 illustrates an embodiment of a Therapeutic-GARD wherein the thicker nitinol spring ring is incorporated in a silicon ring.
Figure 2A:
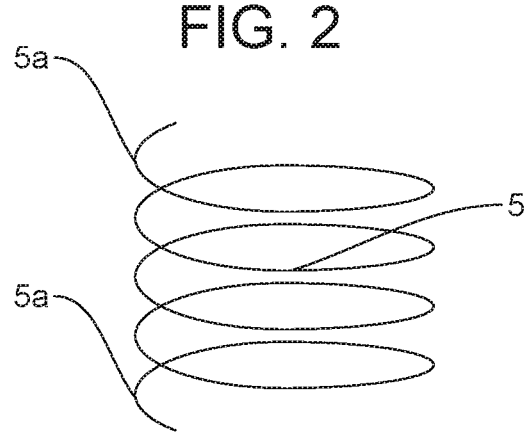

In FIG. 2 the thicker nitinol spring ring 4 incorporated in a silicon ring is shown inside the mesh ring. The nitinol spring ring (2a) rises above the mesh upper part so that it can be removed more easily without displacing the mesh ring that has to be incorporated in the esophageal wall. A detail of the nitinol ring (5) is shown where both ends are curved (5a) to avoid perforation of the overlying silicone ring and possible risk of perforation of the esophageal wall.

Figure 3:
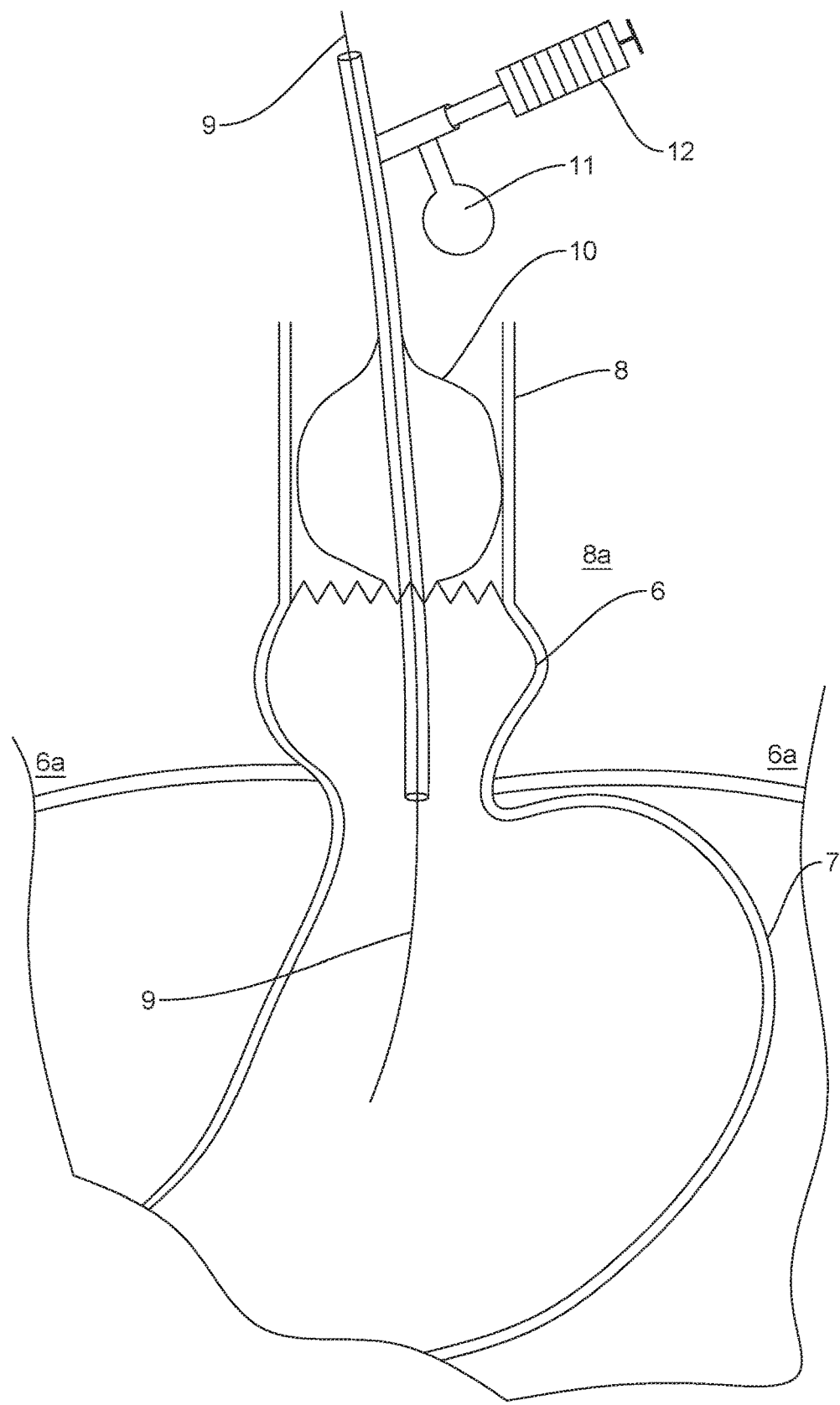
FIG. 3 shows a calibration balloon 10 is with a central catheter above a big guide-wire.

The calibration balloon 10 is shown in FIG. 3 with a central catheter above a big guide-wire (9). The balloon catheter is filled with air or water with a syringe (12) and the air or water pressure that will start to rise when the balloon is in contact with the esophageal wall is controlled with a manometer (11) and/or direct endoscopic visualization. The esophagus is (8), the hiatus hernia often present with more severe GERD is (6) and the stomach (7). The diaphragm is represented by (6a). Normally, the junction of the esophagus and stomach is at the level of the diaphragm or lower in the abdomen. The sliding hiatus hernia (6) represented here is a factor that facilitates and worsens GERD.

The calibration card used illustrated in FIG. 4a has 10 holes with a 1 mm increase of diameter corresponding to the sizes of the mesh net to obtain a mesh net diameter corresponding exactly to the diameter of the patient's esophagus. The numbers under the holes on the calibration card (FIG. 4a) correspond to the diameter of the hole in millimeters (mm). In (4b), the calibration balloon (10) is reinflated to exactly the same diameter as in the esophagus and the exact diameter is determined. If the diameter is in between 2 holes, the larger hole is used to determine the size.

Referring now to FIG. 5, an endoscope (13) with a biopsy catheter (14) is used to make multiple biopsies of the esophageal mucosa (15) above the hiatus hernia. This causes bleeding of the mucosa at all biopsy sites. Alternatively, endoscopic mucosal resection (EMR) or endoscopic submucosal resection (ESD) can be used.

A Therapeutic-GARD shown in FIG. 6 is folded on an introducer catheter (16) that has a central hole for the guide-wire (9). The mesh ring (1) with the nitinol spring ring inside (4 and 5) is kept folded on the introducer catheter with a slip knot (17). The slip knot is a knot that will undo itself simply by pulling on it. A ring (18) or a bead (not shown) is used to pull on the knot to free both rings and place the mesh ring right above the area in the esophagus where the biopsies have been made. A second lower slip knot (17) will hold the tubular anti-reflux valve (2) on the catheter and will be released when the introducer is in position. A third thread passing through both slip knots is used for security and blocks both slip knots to avoid inadvertent release. (not shown).

FIG. 7 illustrates the Therapeutic GARD of FIG. 6 is illustrated in the patient's esophagus. Again, (1) is the outer mesh, (2) the tubular valve, (4) the nitinol spring ring, (8) the esophagus, (9) the guide-wire, (16) the Introducer catheter and (17) the 2 slip knots.

Figure 8A:
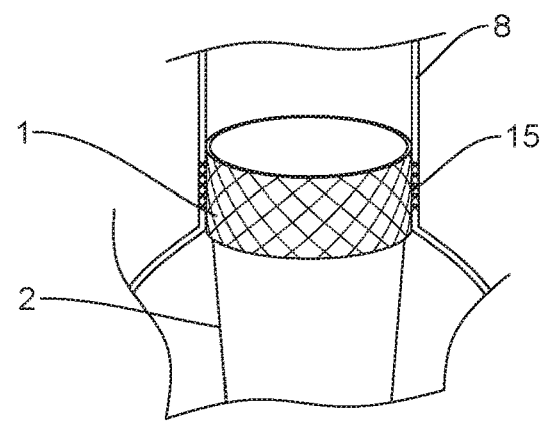

In FIG. 8 the positioning of the mesh ring (1) on the bleeding sites on the esophageal mucosa (15) is demonstrated. (4) is the temporary nitinol spring ring. FIG. 8A shows the effect of the nitinol spring ring (not shown) with lateral arrows demonstrating lateral pressure on the mesh ring to help application and integration of the mesh ring in the esophageal wall at the level of the biopsies (15). (2) is the beginning of the tubular valve.

Injection using an endoscope with an injection catheter (19) of botulinum toxin that blocks peristalsis in the esophageal wall (20) is shown in FIG. 9.

Figure 10:
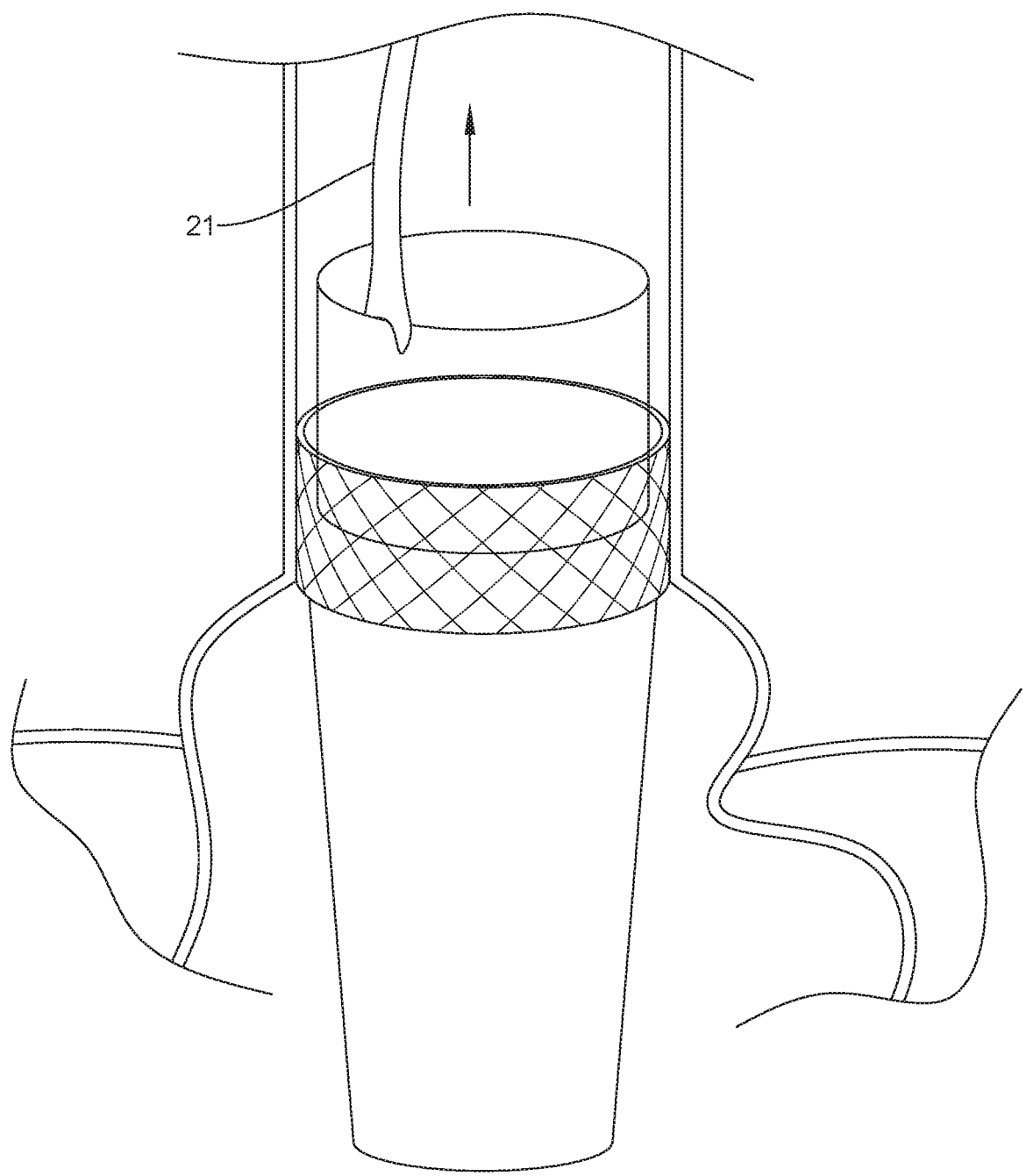
FIG. 10 illustrates a removal catheter used to remove the nitinol spring ring.

FIG. 10 illustrates a removal catheter (21) being used to remove the nitinol spring ring.

FIG. 11 illustrates the mesh ring (1) integrated in the esophageal wall with a tubular valve (2).

Figure 11C:
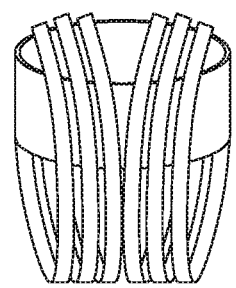

FIG. 11b illustrates a device with a slit valve (22) allowing vomiting as shown when the slit valve reverses as in FIG. 11c.

Figure 12:
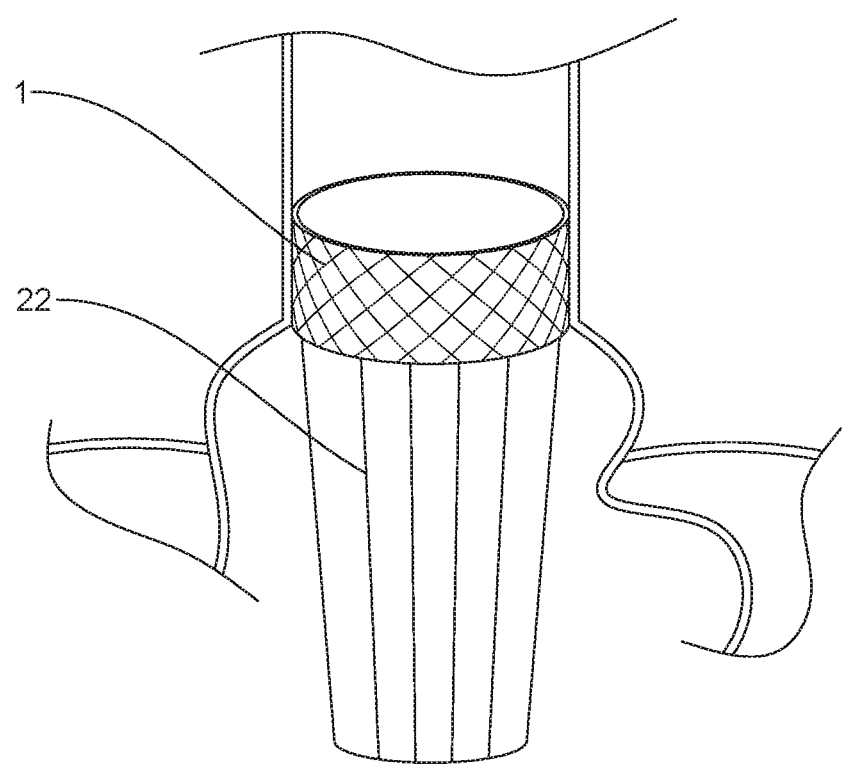
In FIG. 12 the slit valve is shown resuming its original position after vomiting.

FIG. 12 shows the slit valve resuming its original position after vomiting with the mesh (1) in place and the slit valve resuming their original position.

What is claimed is:

1. A prosthesis used for long-term treatment of Gastro-Esophageal Reflux Disease (GERD), the prosthesis comprising:
    an upper thin ring mesh for incorporation in an esophageal wall of a patient with a lower tubular part to block reflux, and
    a removable nitinol spring ring configured to support the upper thin ring mesh and temporarily exert lateral pressure on the upper thin ring mesh.

2. The prosthesis of claim 1, wherein the upper thin ring mesh includes a lower tubular slit part to block reflux and allowing vomiting.

3. The prosthesis of claim 1, wherein the upper thin ring mesh includes a lower longer tube configured to reach into the stomach.

4. The prosthesis of claim 1, wherein the prosthesis is configured to calibrate a diameter of the esophagus using a calibration balloon with a manometer and a calibration card with at least 10 different sizes.

5. The prosthesis of claim 1, wherein the lower tubular part is kept in place for incorporation in the esophagus after bleeding of the esophagus has been caused by esophageal biopsies, endoscopic mucosal resection or endoscopic submucosal resection or a combination thereof.

6. The prosthesis of claim 1, the nitinol spring ring is configured to be kept in place by injection of botulinum toxin in the esophageal wall to block locally esophageal peristalsis during the time needed for incorporation of the mesh ring in the wall of the esophagus.

* * * * *